United States Patent [19]

Taniuchi et al.

[11] Patent Number: 5,007,955

[45] Date of Patent: Apr. 16, 1991

[54] CATIONIC HERBICIDES

[75] Inventors: Akira Taniuchi, Kyoto; Hironori Kataoka, Ikoma; Etsuo Ito, Kyoto, all of Japan

[73] Assignee: Dai-Ichi Kogyo Seiyaku Co., Ltd., Kyoto, Japan

[21] Appl. No.: 267,705

[22] Filed: Nov. 4, 1988

Related U.S. Application Data

[63] Continuation of Ser. No. 110,389, Oct. 20, 1987, abandoned.

[51] Int. Cl.$^5$ ............................................. A01N 41/04
[52] U.S. Cl. .......................................... 71/103; 71/121
[58] Field of Search .................................. 71/103, 121

[56] References Cited

U.S. PATENT DOCUMENTS

| | | | |
|---|---|---|---|
| 3,482,961 | 12/1969 | Nickell et al. | 71/121 |
| 3,506,432 | 4/1970 | Abramitis et al. | 71/121 |
| 3,632,330 | 1/1972 | Michaelson | 71/121 |
| 3,807,983 | 4/1974 | Abramitis | 71/121 |
| 3,884,670 | 5/1975 | Zeeh et al. | 71/121 |
| 4,266,962 | 5/1981 | Kersting et al. | 71/103 |
| 4,488,901 | 12/1984 | Farkas et al. | 71/121 |

Primary Examiner—Allen J. Robinson
Assistant Examiner—John Pak
Attorney, Agent, or Firm—Millen, White & Zelano

[57] ABSTRACT

A cationic herbicidal composition which contains as an active ingredient a quaternary ammonium salt of the general formula:

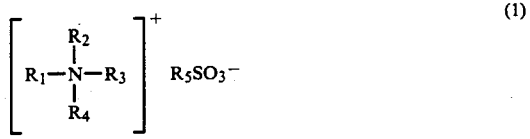

(1)

wherein $R_1$ is an alkyl or alkenyl group of up to 22 carbon atoms; $R_2$ and $R_3$ each is an alkyl or alkenyl group of up to 22 carbon atoms, a benzyl group or a hydroxyalkyl group of up to 4 carbon atoms; $R_4$ is a hydroxyalkyl group of up to 4 carbon atoms; and $R_5$ is an alkyl group of 1 to 22 carbon atoms, a phenyl group, a $C_{1-22}$ alkyl- or hydroxy-substituted phenyl group, or a naphthyl group.

18 Claims, No Drawings

CATIONIC HERBICIDES

This application is a continuation of application Ser. No. 07/110,389, filed Oct. 20, 1987, now abandoned.

BACKGROUND OF THE INVENTION

1. Field of the Invention

This invention relates to a cationic herbicidal composition containing a defined quaternary ammonium salt as an active ingredient, which composition exhibits excellent herbicidal activity.

2. Description of the Prior Art

While a large variety of herbicides have heretofore been developed and used as indispensable materials in the production of crops, there has been an ever more stringent set of requirements in regard to weed killing activity, safety and reduction of phytotoxic effect on useful crop plants.

To meet these rigorous requirements, the present inventors made intensive studies and discovered a herbicidal agent which displays very effective control effects against obstinate weeds without adversely affecting the crop plants. The present invention is the result of further research following the above discovery.

DISCLOSURE OF THE INVENTION

The present invention is directed to a herbicidal composition containing as an active ingredient a quaternary ammonium salt of the general formula:

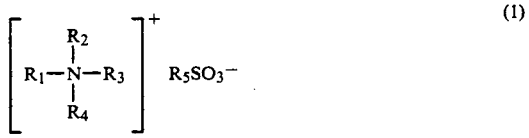

(1)

wherein $R_1$ is an alkyl or alkenyl group of up to 22 carbon atoms; $R_2$ and $R_3$ each is an alkyl or alkenyl group of up to 22 carbon atoms, a benzyl group or a hydroxyalkyl group of up to 4 carbon atoms; $R_4$ is a hydroxyalkyl group of up to 4 carbon atoms; and $R_5$ is an alkyl group of 1 to 22 carbon atoms, a phenyl group, a $C_{1-22}$ alkyl- or hydroxy-substituted phenyl group, or a naphthyl group.

The quaternary ammonium salt of general formula (1) can be produced, for example by the following method. Thus, a compound of general formula (2)

(2)

wherein $R_1$, $R_2$, $R_3$, and $R_4$ are as defined in formula (1); X is a halogen atom and a compound of general formula

$R_5SO_3M$ (3)

wherein $R_5$ is the same as in formula (1); M is an alkali metal or alkaline earth metal are stirred together in the presence of a solvent such as a $C_{1-6}$ straight-chain or branched alcohol, ethyl acetate, dioxane, methyl ethyl ketone, cyclohexanol, etc. at a temperature of 50° to 100° C. for 5 to 24 hours. The reaction mixture is then filtered at 0° to 50° C. to separate the byproduct alkali metal halide and the filtrate is concentrated to give a compound of general formula (1).

Typical examples of the compound of general formula (1) are dodecylmethylbis(hydroxyethyl)ammonium phenolsulfonate, oleylmethylbis(hydroxyethyl)ammonium para-toluenesulfonate, dilaurylbis(hydroxyethyl)ammonium hydroxyethanesulfonate, trimethyl(hydroxyethyl)ammonium dodecylbenzenesulfonate, dilauryl(hydroxyethyl)benzylammonium phenolsulfonate and laurylbis(hydroxyethyl)allylammonium naphthalenesulfonate.

The cationic herbicides provided by this invention display particularly excellent control activity against velvet leaf, pigweed, wild mustard, bindweed, Jimson weed, Fall morning glory, wild oat, cheat grass, yellow nutsedge, crab grass, barnyard grass and so on without causing no injurious effect on soybean, sugar cane, cotton, maize, wheat, and rice plants.

The effective amount of the cationic herbicide of this invention is 0.1 to 5 Kg/ha for selective control and may be greater than the above range for total control.

The herbicide according to this invention or a composition thereof can be applied in such application forms as dusts, granules, wettable powders, emulsions, aqueous solutions and so on as formulated with a liquid and/or solid excipient or diluent and further with a wetting agent, emulsifying agent and/or dispersing agent.

Preferred examples of said liquid excipients are water, methanol, ethanol, toluene, xylene, cyclohexane, isophorone, n-paraffin, and so on, while preferred examples of said solid excipients include bentonite, talc, clay, kaolin, calcium carbonate, white carbon, and so on.

As the surfactants which are used for purposes of wetting, emulsification and dispersion, there may be mentioned nonionic surfactants such as polyoxyethylene alkylaryl ether, polyoxyethylenesorbitan monolaurate, etc., cationic surfactants such as alkyldimethylbenzylammonium chloride, alkyl-pyridinium chloride, etc., and amphoteric surfactants such as alkyldimethylbetaine, dodecylaminoethylglycine and so on.

In applying the herbicide according to this invention in the form of an emulsion, a mixture of 10 to 50 weight parts of the compound of this invention with 10 to 40 weight parts of a solvent and 5 to 20 weight parts of a surfactant (emulsifiable concentrate) is diluted with water.

In the case of a wettable powder, a mixture of 10 to 50 weight parts of the compound of this invention, 10 to 40 weight parts of a volume builder and 2 to 10 weight parts of a surfactant is diluted with water for application.

In the case of dusts, a mixture of 1 to 5 weight parts of the compound of this invention and 90 to 95 weight parts of an inorganic carrier can be directly applied.

The following examples are further illustrative of this invention and should by no means be construed as limiting its scope.

EXAMPLE 1

A 4-necked flask fitted with a stirrer and cooling condenser was charged with 39 g of oleylmethylbis(hydroxyethyl)ammonium chloride, 22 g of potassium p-toluenesulfonate and 200 g of isobutyl alcohol and under a small amount of nitrogen gas, the reaction was conducted at 40°–50° C. for 6 hours. The precipitate thus formed was separated and washed with 30 ml of isobutyl alcohol and the filtrate and washings were concentrated under reduced pressure. The concentrate was dissolved in 200 ml of acetone and after the insoluble matter was filtered off, the acetone was distilled off.

Yield of the concentrate 51 g (calcd. 52.7 g)

From the results shown in Table 2, it can be confirmed that the herbicidal compositions according to the invention are not phytotoxic to crop plants such as soybean, potato, rice, maize and sugar cane.

Table 1

| | Compound | Evaluation | | | |
|---|---|---|---|---|---|
| | | Ve | Bi | Ye | Ba |
| According to the invention | Dodecylmethylbis (hydroxyethyl) ammonium phenolsulfonate | 5 | 5 | 5 | 5 |
| | Oleylmethylbis (hydroxyethyl) ammonium, para-toluenesulfonate | 5 | 5 | 5 | 5 |
| | Dilaurylbis (hydroxyethyl) ammonium hydroxyethanesulfonate | 5 | 5 | 5 | 5 |
| | Trimethyl (hydroxyethyl) ammonium dodecylbenzenesulfonate | 5 | 5 | 5 | 5 |
| | Dilauryl (hydroxyethyl) benzylammonium phenolsulfonate | 5 | 5 | 5 | 5 |
| | Laurylbis (hydroxyethyl) allylammonium naphtalenesulfonate | 5 | 5 | 5 | 5 |
| For comparison | 4-Amino-6-tert-butyl-4,5-dihydro-3-methylthio-1,2,4-triazine | 5 | 3 | 5 | 2 |

TABLE 2

| | Compound | Evaluation | | | | |
|---|---|---|---|---|---|---|
| | | Soybean | Potato | Rice | Maize | Sugar cane |
| According to the invention | Dodecylmethylbis (hydroxyethyl) ammonium phenolsulfonate | 10 | 10 | 10 | 10 | 10 |
| | Oleylmethylbis (hydroxyethyl) ammonium part-toluenesulfonate | 10 | 10 | 10 | 10 | 10 |
| | Dilaurylbis (hydroxyethyl) ammonium hydroxyethanesulfonate | 10 | 10 | 10 | 10 | 10 |
| | Trimethyl (hydroxyethyl) ammonium dodecylbenzenesulfonate | 10 | 10 | 10 | 10 | 10 |
| | Dilauryl (hydroxyethyl) benzylammonium phenolsulfonate | 10 | 10 | 10 | 10 | 10 |
| | Laurylbis (hydroxyethyl) allylammonium naphtbalenesulfonate | 10 | 10 | 10 | 10 | 10 |
| For comparison | 4-Amino-6-tert-butyl-4,5-dihydro-3-methylthio-1,2,4-triazine | 8 | 5 | 3 | 6 | 4 |
| | Untreated | 10 | 10 | 10 | 10 | 10 |

Analysis for oleylmethylbis(hydroxyethyl)ammonium p-toluenesulfonate:

Cl:0.01%,
$SO_3$: 15.31% (calcd. 15.18),
C:65.91% (calcd. 66.03),
H:9.60% (calcd. 10.07),
O:15.26% (calcd. 15.18).

In the same manner as above, the compounds listed in Table 1 were produced.

EXAMPLE 2

In a greenhouse, the test plants velvet leaf (Ve), bind weed (kBi), yellow nutsedge (Ye) and barnyard grass (Ba) were sprayed with an aqueous solution (500 liters/ha) of each of the active ingredients according to the invention which are given in Table 1 on the 14th day after germination at a dose of 3 kg active ingredient/ha, and the results of the treatment were evaluated in terms of scores 0–5 seven days after treatment.

The results thus obtained are shown in Table 1.
0:No effect.
5:The plant was killed.

From the results shown in Table 1, it can be confirmed that the herbicidal compositions according to the invention produce remarkable herbicidal effects.

EXAMPLE 3

In a greenhouse, the plants shown in Table 2 were treated, after germination, with aqueous dilutions of the herbicidal ingredients according to the invention at a dose of 0.4 kg/ha. One week later, the treatment results were evaluated in terms of scores 0–10.

The results thus obtained are shown in Table 2.
0:The plant was completely killed.
10:No effect.

What is claimed is:

1. A method of combatting weeds which comprises applying thereto a herbicidally effective amount of a cationic herbicidal composition which contains as an active ingredient a quaternary ammonium salt of the general formula:

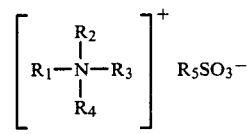

wherein $R_1$ is an alkyl or alkenyl group of up to 22 carbon atoms; $R_2$ and $R_3$ each is an alkyl or alkenyl group of up to 22 carbon atoms, a benzyl group or a hydroxyalkyl group of up to 4 carbon atoms; $R_4$ is a hydroxyalkyl group of up to 4 carbon atoms; and $R_5$ is an alkyl group of 1 to 22 carbon atoms, a phenyl group, a $C_{1-22}$ alkyl- or hydroxy-substituted phenyl group, or a naphthyl group.

2. A method of claim 1, wherein $R_5$ is phenyl, $C_{1-22}$-alkyl or hydroxy-substituted phenyl or naphthyl.

3. A method of claim 1, wherein $R_5$ is dodecylphenyl.

4. A method of claim 1, wherein $R_1$ is dodecyl, oleyl or laurel.

5. A method of claim 4, wherein $R_2$ and $R_3$ are methyl or hydroxyethyl.

6. A method of claim 1 wherein said quaternary ammonium salt is dodecylmethylbis(hydroxyethyl)ammonium phenolsulfonate.

7. A method of claim 1 wherein said quaternary ammonium salt is oleylmethylbis(hydroxyethyl)ammonium para-toluenesulfonate.

8. A method of claim 1 wherein said quaternary ammonium salt is dilaurylbis(hydroxyethyl)ammonium hydroxyethanesulfonate.

9. A method of claim 1 wherein said quaternary ammonium salt is trimethyl(hydroxyethyl)ammonium dodecylbenzenesulfonate.

10. A method of claim 1 wherein said quaternary ammonium salt is dilauryl(hydroxyethyl)benzylammonium phenolsulfonate.

11. A method of claim 1 wherein said quaternary ammonium salt is laurylbis(hydroxyethyl)allylammonium naphthalenesulfonate.

12. A method of claim 1, wherein said cationic herbicidal composition is an aqueous emulsion containing a mixture of 10 to 50 parts of said quaternary ammonium salt, 10 to 40 weight parts of a solvent and 5 to 20 weights parts of a surfactant.

13. A method of claim 12, wherein said quaternary ammonium salt is dodecylmethylbis(hydroxyethyl) ammonium phenolsulfonate, oleylmethylbis(hydroxyethyl)ammonium para-toluenesulfonate, dilaurylbis(hydroxyethyl)ammonium hydroxyethanesulfonate, trimethyl(hydroxyethyl)ammonium dodecylbenzenesulfonate, dilauryl(hydroxyethyl)benzylammonium phenolsulfonate or laurylbis(hydroxyethyl)allylammonium naphthalenesulfonate.

14. A method of claim 1, wherein said cationic herbicidal composition is a wettable powder mixture of 10 to 50 weight parts of said quaternary ammonium salt, 10 to 40 weight parts of a volume builder and 2 to 10 weight parts of a surfactant.

15. A method of claim 14, wherein said quaternary ammonium salt is dodecylmethylbis(hydroxyethyl)ammonium phenolsulfonate, oleylmethylbis(hydroxyethyl)ammonium para-toluenesulfonate, dilaurylbis(hydroxyethyl)ammonium hydroxyethanesulfonate, trimethyl(hydroxyethyl)ammonium dodecylbenzenesulfonate, dilauryl(hydroxyethyl)benzylammonium phenolsulfonate or laurylbis(hydroxyethyl)allylammonium naphthalenesulfonate.

16. A method of claim 1, wherein said cationic herbicidal composition is a dust mixture of 1-5 weight parts of said quaternary ammonium salt and 90 to 95 weight parts of an inorganic carrier.

17. A method of claim 16, wherein said quaternary ammonium salt is dodecylmethylbis(hydroxyethyl)ammonium phenolsulfonate, oleylmethylbis(hydroxyethyl)ammonium para-toluenesulfonate, dilaurylbis(hydroxyethyl)ammonium hydroxyethanesulfonate, trimethyl(hydroxyethyl)ammonium dodecylbenzenesulfonate, dilauryl(hydroxyethyl)benzylammonium phenolsulfonate or laurylbis(hydroxyethyl)allylammonium naphthalenesulfonate.

18. A method of claim 1, wherein said weed is velvet leaf, pigweed, wild mustard, bindweed, Jimson weed, Fall morning glory, wild oat, cheat grass, yellow nutsedge, crabgrass or barnyard grass.

* * * * *